(12) United States Patent
Dao (10) Patent No.: US 8,580,934 B2
(45) Date of Patent: Nov. 12, 2013

(54) SILICA-BASED MATERIAL FOR DETECTION AND ISOLATION OF CHITIN AND CHITIN-CONTAINING MICROORGANISMS

(75) Inventor: My Lien Dao, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 106 days.

(21) Appl. No.: 12/869,581

(22) Filed: Aug. 26, 2010

(65) Prior Publication Data

US 2011/0053187 A1    Mar. 3, 2011

Related U.S. Application Data

(60) Provisional application No. 61/236,989, filed on Aug. 26, 2009.

(51) Int. Cl.
    *A61K 31/722*      (2006.01)

(52) U.S. Cl.
    USPC .......................................................... 530/412

(58) Field of Classification Search
None
See application file for complete search history.

(56) References Cited

PUBLICATIONS

Samie et al. (Trans R. Soc. Trop. Med. Hyg., 101:547-554, 2007).*
Novikov (Russian J. Appl. Chem., 77:484-487, 2004).*

* cited by examiner

*Primary Examiner* — Brian J Gangle
(74) *Attorney, Agent, or Firm* — Saliwanchik, Lloyd & Eisenschenk (57) ABSTRACT

The subject invention provides silica-based material that has high affinity to chitin, chitin derivatives and chitin-containing microorganisms at an acidic pH. In an embodiment, the silica-based material surface comprises glass. Also provided are methods for preparing the subject silica-based chitin-binding material. In addition, the subject invention provides rapid, specific, sensitive, accurate and convenient methods for detection, isolation and purification of chitin, chitin derivatives and chitin-containing microorganisms.

20 Claims, 6 Drawing Sheets

SILICA-BASED MATERIAL FOR DETECTION AND ISOLATION OF CHITIN AND CHITIN-CONTAINING MICROORGANISMS

CROSS-REFERENCE TO RELATED APPLICATION

The subject application claims the benefit of U.S. Provisional application Ser. No. 61/236,989, filed Aug. 26, 2009, which is incorporated herein by reference in its entirety, including any figures, tables, or drawings.

GOVERNMENTAL SUPPORT

This invention was made with government support under Grant Nos. R21DE014296 and R21DE015127 awarded by the National Institutes of Health. The government has certain rights in the invention.

BACKGROUND OF THE INVENTION

Fungi are ubiquitous opportunistic parasites that infect a variety of species, including humans. Microsporidia, a phylum of unicellular fungi that include over 1200 species, infect a range of hosts. Species of the genus *Encephalitozoon* can disseminate in the host body and infect organs such as intestine, lung, kidney, brain, sinuses, muscles and eyes, and shed spores in feces, tissue, saliva, ocular and nasal discharged fluids, urine, mucus and blood. Microsporidiosis (i.e. microsporidia infection) causes chronic, debilitating diseases, including chronic and profuse diarrhea, electrolyte imbalance, food malabsorption, wasting syndrome, pulmonary microsporidiosis, respiratory failure, and even death. While microsporidia can infect healthy individuals, severe syndromes of microsporidiosis primarily occur in patients with compromised or suppressed immune-system, such as in senior citizens, HIV-infected individuals, cancer patients and organ transplant recipients.

Despite its adverse public health impacts, there lacks an accurate, sensitive, and convenient clinical assay capable of detecting microsporidia infection. As a result, a myriad of diseases associated with microsporidia remain vastly underdiagnosed. Common clinical assays include serological tests, transmission electron microscopy, histochemical methods, immunofluorescence, and polymerase chain reaction (PCR); however, all of them exhibit significant shortcomings. Serological tests produce high false-positive results in immunodeficient individuals, who are often incapable of eliciting adequate and specific immune responses. Histochemical staining methods also produce high false-positive results in detecting microsporidia infection, since the commonly used dyes such as Calcofluor white, Fungi-fluor and Uvitex 2B stain a variety of fungi species indiscriminately. While transmission electron microscopy may accurately detect microsporidia, it is time-consuming and thus not practical for routine clinical uses. Similarly, immunofluorescence and PCR require special equipment and trained personnel, and thus, have limited applications beyond most research laboratories.

In addition, there is a lack of efficient techniques for detection or removal of microsporidia spores from environmental samples. For instance, in a publication by Hoffman R. M. et al., it was shown that continuous flow centrifugation only recovered 38.7-75.5% of microsporidia *Encephalitozoon intestinalis* seeded in filtered tap water. While immunomagnetic bead separation (IMS) enables a higher recovery of 78.8-90.2%, such recovery can be only obtained from certain environmental samples such as seeded ultrapure water samples, but can not be obtained from turbid samples. In addition, as particles that may interfere with PCR commonly exist in environmental samples and fungal spores, the combination of IMS and real-time PCR only detected six of the ten natural water samples seeded with 50 spores per L. Therefore, improved techniques for detection, isolation and/or removal of microsporidia as well as other pathogenic fungi species are urgently needed.

BRIEF SUMMARY OF THE INVENTION

The aforementioned need is satisfied by the subject invention, providing novel silica-based material that has high affinity to chitin, chitin derivatives, and chitin-containing microorganisms (such as microsporidia) at an acidic pH, preferably at a pH of about 2.0 to about 5.0. In an embodiment, the material has a surface that comprises silica (also known as silicon dioxide), having a chemical formula of $SiO_2$. In an embodiment, the silica-based material surface comprises glass. Also provided are methods for preparing the subject silica-based chitin-binding material.

In a preferred embodiment, the subject material is packed into a chromatographic column as solid phase sorbent material. In a specific embodiment, the solid phase sorbent material comprises glass beads, glass fiber, and/or other glass matrices. Also provided are methods for preparing the chromatographic column for isolation, purification, and/or detection of chitin, chitin derivatives, and chitin-containing microorganisms.

In addition, the subject invention provides rapid, specific, sensitive, accurate and convenient methods for detection, isolation, and purification of chitin, chitin derivatives and chitin-containing microorganisms. The methods are especially useful for separation and/or removal of such microorganisms from a variety of samples such as water, aqueous solutions, turbid samples, biological samples, bodily fluids, blood, solutions of pharmaceutical products, and other compounds of biological origin. Also provided are diagnostic assays for rapid and accurate detection of infection with chitin-containing microorganisms.

Chitin-containing microorganisms isolated according to the subject invention can be detected using currently available methods including, but not limited to, in-situ immunochemical staining, Western blots, enzyme-linked immunosorbent assay (ELISA), immunoprecipitation, immunofluorescence, radioimmunoassay, and immunocytochemistry. The chitin-containing microorganisms can also be isolated, stained, and observed under microscopy.

In certain embodiments, the subject diagnostic assay can be used to detect infection with fungi species selected from the phyla of Blastocladiomycota, Chytridiomycota, Glomeromycota, Microsporidia, and Neocallimastigomycota; pathogenic fungi species such as *Stachybotrys, Pneumocystis, Cryptococcus, Aspergillus,* and *Candida* species; and microsporidia species such as *Brachiola algerae, B. connori, B. vesicularum, Encephalitozoon cuniculi, E. hellem, E. intestinalis, Enterocytozoon bieneusi Microsporidium ceylonensis, M. africanum, Nosema ocularum, Pleistophora* sp., *Trachipleistophora hominis, T. anthropophthera, Vittaforma corneae,* and *Encephalitozoon intestinalis.*

Further provided are materials and methods for isolation, purification, separation, removal, and/or detection of chitin, chitin derivatives, and chitin-containing microorganisms. Also provided are kits for diagnosis of diseases associated with infection of chitin-containing pathogenic microorganisms. In an embodiment, the kit comprises a material having a surface that comprises silica. In certain embodiments, the subject silica-based material can be used to produce test strips, slides, affinity columns, capillary tubes, coated tubes, microtiter wells or plates, membranes, filters, dot blot matrices, beads, resins, or fibers.

BRIEF DESCRIPTION OF THE DRAWINGS

FIG. 2 shows detection of microsporidia *Encephalitozoon* spores in blood samples by in-situ immunochemical staining of spores hound to glass fibers. Spores were isolated from blood samples using affinity chromatographic columns packed with glass heads. Isolated spore suspension was then loaded onto columns packed with glass fibers, followed by in-situ immunochemical staining of the spores. Specifically, spores were incubated with a primary antibody that detects microsporidia *Encephalitozoon* and a secondary antibody (an alkaline-phosphatase-conjugated antibody) that detects the primary antibody. Color was developed via incubation of the antibody-bound spores with a substrate for alkaline phosphatase. Samples containing microsporidia developed pink to dark red colors. The samples with dark red color contained higher numbers of microsporidia spores.

DETAILED DISCLOSURE OF THE INVENTION

The subject invention provides silica-based material that has high affinity to chitin, chitin derivatives, and chitin-containing microorganisms at an acidic pH. In an embodiment, the material has a surface that comprises silica (also known as silicon dioxide), having a chemical formula of $SiO_2$. In an embodiment, the silica-based material surface comprises glass. Also provided are methods for preparing the subject silica-based chitin-binding material.

Further, the subject invention provides rapid, specific, sensitive, accurate and convenient methods for detection, isolation and purification of chitin, chitin derivatives, and chitin-containing microorganisms. The methods are especially useful separation and/or removal of chitin-containing microorganisms from a variety of samples such as water, aqueous solutions, turbid samples, biological samples, bodily fluids, blood, solutions of pharmaceutical products and other compounds of biological origin. Also provided are diagnostic assays for rapid and accurate detection of infection with chitin-containing microorganisms.

The subject invention is based, at least in part, on the surprising discovery that chitin and chitin-containing microorganisms (e.g., microsporidia) bind to silica (such as glass) at an acidic pH and become detached at a basic pH. Chitin is a common structural component of many microorganisms including fungi. As demonstrated in the Examples, microsporidia *Encephalitozoon* binds to acid-treated glass with high affinity.

In an embodiment, the subject invention provides affinity chromatographic columns for isolation and detection of chitin-containing microorganisms such as microsporidia. In a specific embodiment, glass beads, glass fibers and/or glass matrix are packed into the columns as solid phase sorbent material. The method is rapid (around 10 minutes each), specific and sensitive. Microsporidia spores were successfully isolated from environmental samples, such as natural turbid water samples from Sweetwater Creek and air filter circle rinsed with PBS. Microsporidia spores were also isolated from biological samples, such as blood samples obtained from individuals with asthma-like symptoms, psoriatic arthritis, and healthy volunteers.

Silica-Based Chitin-Binding Material

A first aspect of the subject invention provides silica-based material, which binds to chitin and/or chitin derivatives with high affinity. The subject silica-based material also binds to chitin-containing microorganisms (e.g., fungi species). In an embodiment, the material has a surface that comprises silica (also known as silicon dioxide), having a chemical formula of $SiO_2$, wherein the silica surface has an acidic pH. In an embodiment, the silica-based material surface comprises glass.

It is discovered that chitin, chitin derivatives, and chitin-containing microorganisms bind to silica (e.g., glass) at an acidic pH and becomes unbound at a basic pH. The optimal pH condition for binding and elution of the chitin-containing microorganisms depends on their chitin content. Usually, for efficient binding of the microorganism to the silica-based material, the material surface has an acidic pH. In certain embodiments, the material surface has a pH of about 2.0 to about 6.9, about 2.0 to about 5.0, about 2.5 to about 4.5, about 2.5 to about 3.5, about 3.0 to about 4.0, about 3.0 to about 5.0, or any pH values therebetween. In an embodiment, the material surface may even have a pH of below 2.0. In certain embodiments, the material surface may have a neutral or slightly alkaline pH, such as from about 7.0 to 8.0, about 7.0 to about 7.8, about 7.0 to about 7.5, about 7.0 to about 7.3, or about 7.0 to about 7.1.

Usually, for efficient elution of the microorganism from the silica-based material, the material surface has an alkaline pH. In certain embodiments, the material surface has a pH of about 7.1 to about 10.5, about 7.1 to about 7.5, about 7.5 to about 10.0, about 7.5 to about 9.5, about 7.5 to about 9.0, about 7.5 to 8.5, about 7.5 to 8.0, or any pH values therebetween. In a preferred embodiment, the material surface has a pH of about 7.5 to about 8.5, or about 8.0 during elution. The elution may be performed at a pH more basic than 10.5.

Silica is typically surface-terminated with silanols (—(SiOH)). The oxygen of the hydroxyl group of —(SiOH) becomes protonated at an acidic pH and depotonated at a basic pH. It is thus contemplated that chitin, chitin-derivatives, and chitin-containing microorganisms bind to protonated —(SiOH).

The term "bind" refers to direct attachment of a compound, composition or microorganism to a substrate. In certain cases, such attachment forms a compound/composition/microorganism-substrate complex. Such attachment may be temporary and may involve chemical bonding, electrostatic interaction, hydrogen bond, and/or the van der Waals force.

In an embodiment, at least part of the silica-based chitin-binding material is surface-terminated with silanols. Silanols attached to the silica surface have a general formula of —(SiR$_X$(OH)$_{3-X}$), wherein X is an integer from 0 to 2. Additionally or alternatively, the silica-based chitin-binding material can be chemically modified with a surface-terminating agent, such as for example, silanes and siloxanes. As a result, at least part of the chemically modified surface is terminated with the surface-terminating agent, and wherein the chemically modified surface binds to chitin and/or chitin-derivatives. Silanes attached to the silica surface have a general formula of —(SiR$_X$(H)$_{3-X}$), wherein X is an integer from 0 to 3. Siloxanes attached to the silica surface have a general formula of —(SiR$_X$(O)$_{3-X}$), wherein X is 1 or 2.

In certain embodiments, R is —H, —OH, —O, alkyl, substituted alkyl (e.g., haloalkyl, alkylamino, alkyl alcohol), halo, aromatic, cycloalkyl, alkoxy, aryl, or organofunctional.

The term "alkyl" as used herein refers to a branched or unbranched saturated hydrocarbon group of 1 to 24 carbon atoms, such as methyl ("Me"), ethyl ("Et"), n-propyl, isopropyl, n-butyl, isobutyl, t-butyl, octyl, decyl, tetradecyl, hexadecyl, eicosyl, tetracosyl, and the like. The term "cycloalkyl" intends a cyclic alkyl group from three to eight, preferably five or six carbon atoms. "Alkyl alcohol" refers to alkyl having attached thereto one or more hydroxy moieties, such as, but not limited to, —CH$_2$CH$_2$OH, CH$_2$CH(OH)CH$_3$, CH$_2$OH, CH$_2$CH$_2$CH$_2$OH, CH$_2$CH$_2$CH(OH)CH$_3$, CH$_2$CH$_2$CH(OH)CH$_2$OH, or CH$_2$CH(OH)CH(OH)CH$_3$. The term "small chain alkyl" refers to methyl, ethyl, propyl, and butyl.

The term "alkoxy" as used herein intends an alkyl group bound through a single terminal ether linkage; that is, an "alkoxy" group may be defined as —OR$_a$ where R$_a$ is alkyl as defined above. "Polyether" refers to a compound or moiety possessing multiple ether linkages, such as, but not limited to, polyethylene glycols or polypropylene glycols. "Polyalkylethers" refers to alkyls interconnected by or otherwise possessing multiple ether linkages.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyls and lower alkyls where there is substitution.

The term "aryl" as used herein refers to a compound or moiety whose molecules have a ring or multiple ring structure characteristic of benzene, naphthalene, phenanthrene, anthracene, etc., such as, either the six-carbon ring of benzene or the condensed six-carbon rings of the other aromatic derivatives, including, but not limited to phenyl, benzyl, naphthyl, benzylidine, xylil, styrene, styryl, phenethyl, phenylene, benzenetriyl, etc.

The term "halo" means fluoro, chloro, bromo, or iodo.

As used herein, the term "aromatic" refers to the group of unsaturated cyclic hydrocarbons, typified by benzene, having a 6-carbon ring containing three double bonds or multiple attached benzene rings. Moreover, certain five membered cyclic compounds, such as furan (heterocyclic), are analogous to aromatic compounds. Aromatics include the cyclic compounds based upon a benzene functionality, as specified for "aryl" above.

Moreover, the term "cyclic" is used to refer to all aliphatic or aromatic hydrocarbons having one or more closed rings, whether unsaturated or saturated. Preferably, cyclic compounds possess rings from 5 to 7 carbon atoms, preferably 6 carbon atoms. Such rings fall into three classes: alicyclic, aromatic ("arene"), and heterocyclic. Moreover, when used with respect to cyclic compounds or moieties, the term "unsaturated" refers to such compound or moiety possessing at least one double or triple bond or otherwise constituting an aromatic compound or moiety. Moreover, the term "saturated" refers to compounds or moieties possessing no double or triple bonds, that is, where all available valence bonds of an atom, especially carbon, are attached to other atoms.

The term "heteroaryl" refers to an aryl where one or more of the carbon atoms of a ring have been substituted with a heteroatom, including, but not limited to, O, N, or S.

Similarly, the term "heterocyclic" refers to a cyclic compound or moiety where one or more of the carbon atoms of the ring have been substituted with a heteroatom, including, but not limited to O, N, or S.

As used herein, "substituted" is used to refer, generally, to a carbon or suitable heteroatom having a hydrogen or other atom removed and replaced with a further moiety. In one embodiment, halogen, hydroxy, and nitrogen-based substitutions of hydrocarbon hydrogens are contemplated as within the scope of the present invention for the claimed structures. Moreover, it is intended that "substituted" refer to substitutions which do not change the basic and novel utility of the underlying compounds, products, or compositions of the present invention.

"Unsubstituted" refers to a structure wherein the reference atom does not have any further moieties attached thereto or substituted therefor.

As used herein, "branched" is used to refer, generally, to a moiety having a carbon chain backbone, for example, alkyl or alkoxy, wherein the backbone may contain one or more subordinate carbon chain branches. For example, isobutyl, t-butyl, isopropyl, CH$_2$CH$_2$C(CH$_3$)(H)CH$_2$CH$_3$, CH$_2$C(CH$_2$CH$_3$)(H)CH$_2$CH$_3$, CH$_2$CH$_2$C(CH$_3$)CH$_3$, and CH$_2$CH$_2$C(CH$_3$)$_3$ would all be considered branched moieties. Moreover, it is intended that "branched" variations of the moieties herein described refer to variations that do not change the basic and novel utility of the underlying compounds, products, or compositions of the present invention.

"Unbranched" refers to a structure wherein the carbon chain does not have any branches thereon, that is, where the carbon chain extends in a direct line.

As used herein, the term "acyl" refers to organic acid derived moieties of the formula RCOX where R is an organic molecule and X, instead of being hydroxy, is replaced with another substituent, preferably a suitable anion, such as a halogen including, but not limited to, F, Cl, Br, or I.

As used herein, the term "perfluoro" or "perfluoro-analog" refers to a hydrocarbon where the hydrogen atoms attached to carbons have been replaced with F atoms. Preferably, but not necessarily, in perfluoro-analogs, most, if not all, of the H atoms are replaced with F atoms. A "fluoro-" analog is contemplated to indicate a hydrocarbon where at least one hydrogen atom attached to a carbon is replaced with an F atom.

The silica-based chitin-binding material can be, or be derived from, various silica-containing substances including, but not limited to, glass, colloidal silica, fibrous silica, and silica gel. The silica-based chitin-binding material can also be, or be derived from, silica-containing substances such as ceramics, earthenware, stoneware, and porcelain. Preferably, the silica-based material is non-crystalline, solid material.

In preferred embodiments, the silica-based chitin-binding material is, or is derived from, glass. Suitable glass includes pure silica and silica glass with chemical modifications, such as borate glass and phosphate glass, which can be readily obtained from various commercial sources, such as from Sigma-Aldrich Corporation, Inc., and Corning, Inc.

In addition, the silica-based chitin-binding material (e.g., glass) can be in a variety of forms, such as beads, fibers, particles, and matrices. In certain embodiments, the silica-based chitin-binding material comprises glass beads, having a diameter of about 10-2000 µm, about 50-1800 µm, about 100-1500 µm, about 150-1000 µm, about 200-800 µm, about 300-700 µm, or about 400-500 µm. In another embodiment, the silica-based chitin-binding material comprises glass fiber. In another embodiment, the silica-based chitin-binding material comprises glass beads, glass fiber, and/or glass matrix.

Advantageously, the subject silica-based material has high binding affinity to chitin at an acidic pH. Chitin is a polymer of N-acetyl-D-glucosamine units. The subject silica-based material can also bind to chitin derivatives. Chitin derivatives include polymers (usually composed of >50 monomer units) of β-(1-4)-linked D-glucosamine units and/or polymers of alkyl-substituted β-(1-4)-linked D-glucosamine units. In an embodiment, the subject silica-based material binds to chitosans, which are composed of randomly distributed β-(1-4)-linked D-glucosamine (deacetylated unit) and N-acetyl-D-glucosamine (acetylated unit). Chitin derivatives can be bound by the subject silica-based material also include, such as for example, carboxymethylchitosan, oleoyl chitosan, hydroxypropyl chitosan, and pegylated chitosan. In an embodiment, the subject silica-based material does not bind to cellulose, which is a polymer of β(1→4) linked D-glucose units.

In addition, the subject silica-based material binds to microorganisms that contain chitin, which abundantly exists in the cell walls of fungi species. As demonstrated in the Examples, the subject material binds to chitin-containing microorganism-microsporidia *Encephalitozoon* with high affinity.

The term "microorganism," as used herein, refers to an organism too small to be visualized with the naked eye. Typically, microorganisms have a size of less than 100 µm, 50 µm, 20 µm, or 5 µm. In an embodiment, the microorganism is a fungi species.

In certain embodiments, the subject material binds to chitin-containing microorganisms including, but not limited to, fungi species selected from the phyla of Blastocladiomycota, Chytridiomycota, Glomeromycota, Microsporidia, and Neocallimastigomycota. In certain embodiments, the subject silica-based material binds to one or more pathogenic fungi species including, but not limited to, *Stachybotrys, Pneumocystis, Cryptococcus, Aspergillus*, and *Candida* species.

In a specific embodiment, the subject silica-based material binds to microsporidia species. In certain embodiments, the subject silica-based material binds to one or more pathogenic microsporidia species including, but not limited to, *Brachiola algerae, B. connori, B. vesicularum, Encephalitozoon cuniculi, E. hellem, E. intestinalis, Enterocytozoon bieneusi Microsporidium ceylonensis, M. africanum, Nosema ocularum, Pleistophora* sp., *Trachipleistophora hominis, T. anthropophthera, Vittaforma corneae*, and *Encephalitozoon intestinalis*.

Preparation of Silica-Based Chitin-Binding Material

A second aspect of the invention provides methods for preparing the subject silica-based chitin-binding material. In an embodiment, the method comprises contacting a material with an acidic solution, wherein the material has a surface that comprises silica. In a preferred embodiment, the subject material is packed into a chromatographic column as solid phase sorbent material. In a specific embodiment, the solid phase sorbent material comprises glass beads, glass fiber, and/or glass matrix.

Useful acids include, but are not limited to, acetic, adipic, anisic, arsenic, arsenious, benzoic, boric, bromic, bromous, butanoic, capric, caproic, caprylic, carbonic, chloric, chlorous, chromic, chromous, cinnamic, citric, cyanic, cyanoacetic, diphosphonic, disulfuric, disulfurous, dithionic, dithionous, ferricyanic, ferrocyanic, fluorosilicic, formic, fulminic, fumaric, gallic, glutaric, glycolic, hexadecanoic, hexafluorosilicic, hydrobromic, hydrochloric, hydrocyanic, hydrofluoric, hydroiodic, hydroxybenzoic, hypochlorous, iodic, iodous, isocyanic, isothiocyanic, lactic, lauric, levulinic, maleic, malic, malonic, manganic, molybdic, nitric, nitrous, octadecanoic, oleic, oxalic, pentanoic, valeric, perchloric, periodic, pertechnetic, phosphinic, phosphonic, phosphoric, phthalic, picric, propanoic, pyrogallic, pyruvic, rhenic, salicylic, selenic, selenious, silicic, stearic, succinic, sulfanilic, sulfuric, sulfurous, tartaric, telluric, tellurous, thioacetic, thiocyanic, thiosulfurous, titanic, tungstic, uranic, valeric, and vanillic acids.

Acid concentration and pH can be optimized depending on the chitin content of the microorganism. Usually, the acid treatment is performed at a pH of about 2.0 to about 6.9, about 2.0 to about 5.0, about 2.5 to about 4.5, about 2.5 to about 3.5, about 3.0 to about 4.0, about 3.0 to about 5.0, or any pH values therebetween, while the acid treatment may be performed at a pH below 2.0. Acids can be at a concentration of about 0.1M-1M, about 0.2M to 0.7M, or about 0.3M to about 0.5M. In a specific embodiment, the material surface is treated with 10%, 20%, 30%, 40%, 50%, 60%, 70%, 80%, 90%, or 100% acetic acid.

In an embodiment, the acid treatment is performed by soaking or immersing the silica-based chitin-binding material in acids for a period of about 5 minutes, 10 minutes, 15 minutes, 20 minutes, about 30 minutes, or about 40 minutes. The acid treatment is typically performed under ambient temperature and pressure. Preferably, the acidic solution is removed, washed, or neutralized after the treatment.

In a specific embodiment, the subject invention provides a method for preparing a chromatographic column for isolating chitin, chitin derivatives, and/or chitin-containing microorganisms, comprising:

a) providing a solid phase sorbent material having a surface that comprises silica ($SiO_2$);

b) contacting the material with an acidic solution, whereby the material surface has a pH of less than 7.0 upon contacting the acidic solution; and c) packing a chromatographic column with the material.

Isolation and Detection of Chitin and Chitin-Containing Microorganisms

A third aspect of the invention provides methods for isolation, purification and/or detection of chitin, chitin derivatives, and chitin-containing microorganisms. The methods are especially useful for separation and/or removal of chitin-containing microorganisms from a variety of samples such as water, aqueous solutions, turbid samples, biological samples, bodily fluids, blood, solutions of pharmaceutical products, and other compounds of biological origin.

In an embodiment, the subject invention provides a method for isolation and removal of chitin, chitin derivatives and/or chitin-containing microorganisms. The method comprises:

contacting a sample with a material having a surface that comprises silica, wherein the material surface has an acidic pH, wherein the sample contains chitin, chitin derivative, and/or chitin-containing microorganism, and whereby the chitin, chitin derivative, and/or chitin-containing microorganism binds to the surface and is thereby isolated or removed from the sample.

In a preferred embodiment, the acidic material surface can be obtained by contacting the silica-based material with an acidic solution. In certain embodiments, the acidic solution has a pH of about 2.0 to about 6.9, about 2.0 to about 5.0, about 2.5 to about 4.5, about 2.5 to about 3.5, about 3.0 to about 4.0, about 3.0 to about 5.0, or any pH values therebetween. In an embodiment, the acidic solution has a pH of lower than 2.0.

Chitin, chitin derivatives, and/or chitin-containing microorganisms can be eluted by contacting the silica-based material with an alkaline solution, whereby the chitin, chitin derivatives, and/or chitin-containing microorganisms become detached from the silica-based material and can be recovered from the alkaline solution. In certain embodiments, the alkaline solution has a pH of about 7.1 to about 10.5, about 7.1 to about 7.5, about 7.5 to about 10.0, about 7.5 to about 9.5, about 7.5 to 9.0, about 7.5 to 8.5, about 7.5 to 8.0, or any pH values therebetween. In certain embodiments, the alkaline solution has a pH of about 7.5 to 9.5, about 7.5 to 9.0, about 7.5 to about 8.5, or about 8.0. In an embodiment, the alkaline solution may be at a pH more basic than 10.5. In an embodiment, the alkaline solution comprises Tris and ethylenediaminetetraacetic acid (EDTA).

Chitin-containing microorganisms can be collected or recovered from the alkaline solution by a variety of means, such as by centrifugation. The centrifugation can be performed at from about 300×g to about 15,000×g, about 500×g to about 12,000×g, about 700×g to about 10,000×g, about 1,000×g to about 8,000×g, about 1,500×g to about 5,000×g, or about 2,000×g to about 3,000×g. In certain embodiments, a first centrifugation is performed at from about 100×g to about 500×g, about 150×g to about 500×g, or about 300×g to about 500×g, followed by a second centrifugation at about 1,000×g to about 15,000×g, 1,200×g to about 12,000×g, about 1,500×g to about 10,000×g, about 3,000×g to about 10,000×g, or about 5,000×g to about 7,000×g. The supernatant is discarded and the pellet containing the microorganisms is recovered.

Suitable samples include, but are not limited to, environmental samples such as water, aqueous solutions, turbid samples, biological samples, solutions of pharmaceutical products, and compounds of biological origin. Suitable biological samples include, but are not limited to, bodily fluids, biopsies, mucus, blood, lymph, serum, plasma, urine, saliva, ocular and nasal discharged fluids, cells, tissues, feces, and stool. Tissue samples may include postmortem tissues of intestine, lung, kidney, brain, sinuses, muscles, and/or eyes.

In an embodiment, the subject invention further provides affinity chromatographic columns for isolation, removal and/or detection of chitin, chitin derivatives, and chitin-containing microorganisms. The silica-based material is packed into a cylindrical column as solid phase sorbent material.

Typically, after binding of chitin, chitin derivatives and chitin-containing microorganisms to the silica-based material, the column is washed with buffer solution to remove the last traces of contaminating substances. Washing buffer can have a pH of about 6.5 to about 8.0 or any pH values therebetween, preferably about 7.0 to about 7.5. The pH conditions of the washing step can be optimized based on the chitin content of the microorganisms. Preferably, the washing step does not result in any detectable loss of chitin, chitin derivative and/or chitin-containing microorganisms that are bound to the affinity matrix. In an embodiment, the washing buffer is PBS containing 2% TWEEN 20 (polyoxyethylene (20) sorbitan monolaurate; CAS No 9005-64-5).

In a specific embodiment, the subject invention provides a method for isolating a chitin-containing microorganism, comprising:

a) loading a sample into a chromatographic column that comprises a silica-based material as solid phase sorbent material, wherein the material surface has an acidic pH, and wherein the sample contains chitin, chitin derivative, and/or chitin-containing microorganism;

b) eluting the chitin, chitin derivative, and/or chitin-containing organism by contacting the material with an alkaline solution; and c) recovering the chitin, chitin derivative, and/or chitin-containing microorganism in the alkaline solution.

Optionally, the method further comprises, after step a), washing the column with a buffer solution having a pH of about 7.0-7.5.

Figure 5:
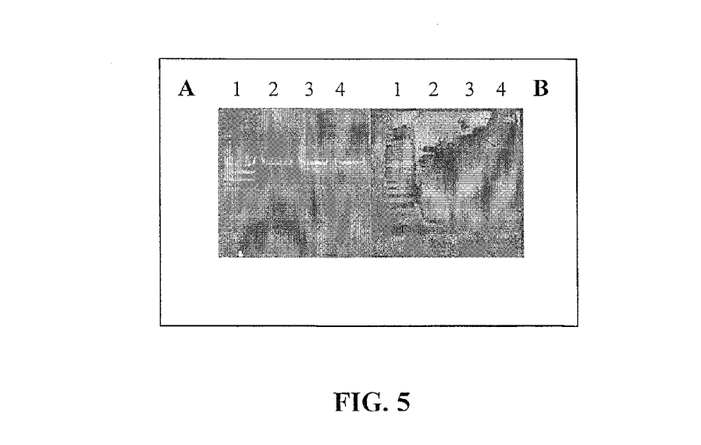
FIG. 5 shows detection of *Encephalitozoon hellem* by polymerase chain reaction (PCR) and agarose gel electrophoresis. PCR product was analyzed by agarose gel electrophoresis. The DNA band obtained corresponded with the control *Encephalitozoon hellem* band. (A) Chromosomal DNA: Lane 1. Lambda phage DNA digested with Hind III; Lane 2. Negative control; Lane 3. DNA of spores isolated from RK13 cells infected with spores isolated from blood samples; Lane 4: DNA of *Encephalitozoon hellem* control; (B) PCR product: Lane 1. 50 base pair ladder; Lanes 2-4: DNA of spores isolated from RK13 cells infected with spores isolated from blood samples of infected individuals. Spores isolated from infected blood samples were confirmed as *Encephalitozoon hellem*.
Figure 6:
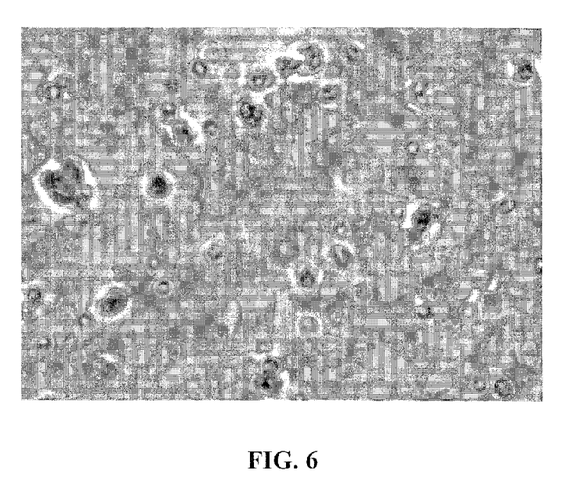
FIG. 6 shows spores of chitin-containing microorganisms isolated from turbid water samples (Sweetwater Creek, Tampa, Fla.). Spores were isolated using affinity chromatographic columns packed with glass beads, and were stained for observation by the methods described in Dao (U.S. Pat. Nos. 7,157,242 and 7,745,168).
Figure 7:
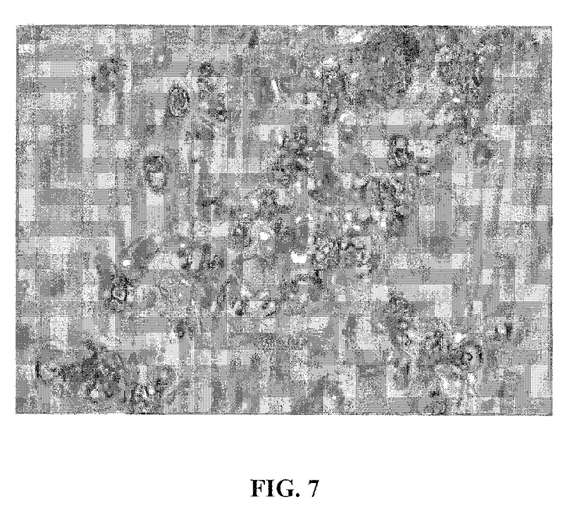
FIG. 7 shows spores of chitin-containing microorganisms isolated from an air filter. Spores were isolated using affinity chromatographic columns packed with glass beads, and were stained for observation by the methods described in Dao (U.S. Pat. Nos. 7,157,242 and 7,745,168).

Chitin-containing microorganisms can also be detected using a variety of methods including, but not limited to, in-situ immunochemical staining, Western blots, Enzyme-linked immunosorbent assay (ELISA), immunoprecipitation, immunofluorescence, radioimmunoassay, immunodot analysis, and immunocytochemistry. The chitin-containing microorganisms can also be isolated, stained and observed under microscopy. Chitin-containing microorganisms can also be detected by amplification of DNA of the isolated microorganisms using polymerase chain reaction (PCR), as shown in FIG. 5.

In an embodiment, chitin-containing microorganisms can be detected using in-situ immunochemical staining method. The method comprises:

loading a sample that has a chitin-containing microorganism onto a material having a surface that comprises silica, wherein the material surface has an acidic pH;

incubating the sample with a primary antibody that detects the chitin-containing microorganism;

incubating the sample with a secondary antibody that detects the primary antibody, wherein the secondary antibody is labeled; and detecting the secondary antibody, wherein the presence of the secondary antibody indicates that the sample has the chitin-containing microorganism.

In a specific embodiment, a sample solution containing *Encephalitozoon* is prepared and loaded on an affinity column packed with glass fiber. The column was washed with PBS containing about 0.05% to about 2%-TWEEN 20 (polyoxyethylene (20) sorbitan monolaurate: CAS No. 9005-64-5), followed by a second wash with PBS containing 10 mM EDTA, and a third wash with PBS-T. The column is incubated with a primary antibody that detects *Encephalitozoon*, followed by a first wash with PBS-T (containing phosphate buffered saline (PBS) and TWEEN 20) and a second wash with a substrate buffer. The column is then incubated with an alkaline phosphatase conjugated secondary antibody that detects the primary antibody. Color development was achieved by in situ staining of the alkaline phosphatase with chromogenic substrate (b-Naphthyl acid phosphate, O dianisidine tetrazotized in sodium phosphate buffer, PH 9.7). A red color is developed and indicates that the sample contains *Encephalitozoon*.

Diagnostic Assays

A fourth embodiment of the invention provides assays for diagnosing diseases associated with infection with pathogenic chitin-containing microorganisms. In an embodiment, the method comprises:

a) obtaining a biological sample from a subject;

b) contacting the biological sample with a material having a surface that comprises silica ($SiO_2$), wherein the material surface has a pH of less than 7.0; and c) determining the presence or absence of the chitin-containing microorganism in the biological sample; and wherein the presence of the chitin-containing microorganism in the biological sample indicates that the subject has infection.

The term "subject," as used herein, describes an organism, including mammals such as primates. Mammalian species that can benefit from the subject methods include, but are not limited to, apes, chimpanzees, orangutans, humans, monkeys; and domesticated and/or laboratory animals such as dogs, cats, horses, cattle, pigs, sheep, goats, chickens, mice, rats, guinea pigs, rabbits and hamsters. Typically, the subject is a human.

In certain embodiments, the subject diagnostic assay can be used to detect infection with fungi species selected from the phyla of Blastocladiomycota, Chytridiomycota, Glomeromycota, Microsporidia, and Neocallimastigomycota; pathogenic fungi species such as *Stachybotrys, Pneumocystis, Cryptococcus, Aspergillus*, and *Candida* species; and microsporidia species such as *Brachiola algerae, B. connori, B. vesicularum, Encephalitozoon cuniculi, E. hellem, E. intestinalis, Enterocytozoon bieneusi Microsporidium ceylonensis, M. africanum, Nosema ocularum, Pleistophora* sp., *Trachipleistophora hominis, T. anthropophthera, Vittaforma corneae*, and *Encephalitozoon intestinalis*.

Kits

A fifth embodiment of the invention provides kits for isolation, purification, separation, removal and/or detection chitin, chitin derivatives and chitin-containing microorganisms. The kits can also be used for diagnosis of diseases associated with infection with chitin-containing microorganisms. In an embodiment, the kit comprises a material having a surface that comprises silica.

In certain embodiments, the subject silica-based material can be used to produce test strips, slides, affinity columns, capillary tubes, coated tubes, microtiter wells or plates, membranes, filters, dot blot matrices, beads, resins, and fibers. In an embodiment, the subject invention provides chromatographic columns that comprise the subject silica-based material. In a specific embodiment, the subject invention provides affinity columns comprising acid-treated glass beads for the isolation of chitin-containing microorganisms. In another specific embodiment, the subject invention provides affinity columns comprising acid-treated glass fiber for the detection of chitin-containing microorganisms using in situ immunological staining methods.

Optionally, the kit may include any material useful for performing the isolation, purification, detection and/or diagnostic methods of the subject invention. For instance, the kit may further comprise agents that are useful for detection or visualization of chitin, chitin derivatives and/or chitin-containing microorganisms. Such agents include antibodies that detect chitin-containing microorganisms, antibodies against the antibodies labeled with an enzyme; a substrate for the enzyme, alkaline phosphatase, chromogenic substrate (b-naphthyl acid phosphate, O dianisidine tetrazotized in sodium phospahte buffer, PH 9.7), Ponceau S (3-hydroxy-4 ((2-sulfo-4-((-4-sulfophenyl(azo)phenyl-)azo)2,7 naphthalenedisulfonic acid tetrasodium salt), and Stains-all([7423-31-6]1-Ethyl-2-[3-(1-ethylnaphtho[1,2-d]thiazolin-2-ylidene)-2-methylpropenyl]-naphto[1,2-d]thiazolium bromide).

The kit may also comprise, e.g., a buffering agent, a preservative, an acid, or an alkalizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions. The kit can also contain a solid support such as microtiter multi-well plates, standards, assay diluent, wash buffer, adhesive plate covers, and/or instructions for carrying out a method of the invention using the kit.

The kit may also comprise reagents for the isolation of DNA and/or mRNA from fungal spores for use in polymerase chain reaction (PCR) or quantitative PCR.

The agent(s) can be packaged with a container for collecting the biological fluid from a patient. When the antibodies or binding partner are used in the kits in the form of conjugates in which a label is attached, such as a radioactive metal ion or a moiety, the components of such conjugates can be supplied either in fully conjugated form, in the form of intermediates or as separate moieties to be conjugated by the user of the kit.

EXAMPLES

Following are examples that illustrate procedures for practicing the invention. These examples should not be construed as limiting. All percentages are by weight and all solvent mixture proportions are by volume unless otherwise noted.

Example 1

Preparation of Chitin-Binding Glass

This Example illustrates methods for preparing chitin-binding glass, which can be used for isolation, purification, removal and/or detection of chitin-containing microorganisms. In an embodiment, chromatographic columns for isolation of chitin-containing microorganism are prepared as follows. Briefly, glass beads purchased from Sigma Chemical Company were washed and boiled in deionized water, and then soaked in 10% acetic acid. The acid-treated beads were then used to pack chromatographic columns. In another embodiment, chromatographic columns useful for detection of chitin-containing microorganisms were prepared by packing glass wool (also known as glass fiber or fiberglass; purchased from Pyrex) into chromatographic columns, followed by soaking the column packed with glass wool in the column in 10% acetic acid.

Example 2

Isolation of Chitin-Containing Microorganisms by Chitin-Binding Glass

This Example illustrates the isolation of chitin-containing microorganisms by chromatographic columns packed with glass beads. Briefly, samples believed to contain chitin-binding microorganisms are diluted at about 0.1:10 to about 1:10 in binding solution, and loaded onto the chitin-binding column packed with glass beads. The column is washed with 3 column volumes of phosphate buffered saline (PBS) or PBS-T that is PBS containing about 0.05% to about 2% TWEEN 20 (polyoxyethylene (20) sorbitan monolaurate: CAS No. 9005-64-5) at pH 7.5. Chitin-containing microorganisms are eluted from the column by applying 3 column volumes of elution buffer (pH 8), consisting of 20 mM Tris, 2 mM EDTA. The elute is centrifuged at 12,000×g for 15 min or until a pellet is formed. The supernatant is discarded, and chitin-containing microorganisms are isolated by recovering the pellet. Optionally, the pellet may be resuspended in PBS to form spore suspension.

Example 3

Detection of Chitin-Containing Microorganisms

This Example illustrates detection of chitin-containing microorganisms such as microsporidia using in-situ immunochemical staining of spores bound to chitin-binding columns packed with glass fiber. Briefly, spores of chitin-containing microorganisms are isolated by using a chitin-binding glass column packed with glass beads, as described in Example 2. The spore suspensions are loaded onto the chitin-binding glass fiber column. The column is washed with 3 column volumes PBS containing about 0.05% to about 2% TWEEN 20 (polyoxyethylene (20) sorbitan monolaurate: CAS No. 9005-64-5), followed by 3 column volumes of PBS-T. The column is then incubated with 1 ml primary antibody (antibody to microsporidia), diluted 1:100-1:1,000 (dilution depends on antibody concentration) in PBS-T. The column is then sequentially washed with 3 column volumes of PBS containing 10 mM EDTA, followed by 3 column volumes of PBS-T. The column is then incubated with 1 ml alkaline phosphatase-conjugated secondary antibody diluted at 1:10,000 in PBS-T. The column is then washed with 3 column volumes of PBS-T, followed by 1 column volume of alkaline phosphatase substrate buffer (sodium borate buffer, pH 9.7, containing magnesium sulfate). After wash, the column is plugged and filled with an alkaline phosphatase chromogenic substrate containing 25 mg beta napthtyl acid phosphate and 2.5 mg O-dianisidine tetrazotized per 100 ml alkaline phosphatase substrate buffer, and sealed to avoid substrate oxidation. As a result, chitin-containing organisms in the column are stained in situ via incubation with the alkaline phosphatase chromogenic substrate. The column is periodically observed to detect color development. Purple-Red coloration indicates that the sample contains chitin-containing microorganisms (such as microsporidia). Yellow-Brown coloration, developed from the oxidation of O-dianisidine, indicates that the sample does not contain chitin-containing microorganisms (such as microsporidia). FIGS. 1-4 and 6-7 show microsporidia spores detected by in situ immunochemical staining.

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

REFERENCES

1. Hoffman R. M., Wolk D. W., Spencer S. K. and Borchardt M. A., Development of a method for the detection of waterborne microsporidia., Journal of Microbiological Methods, 70:312-318 (2007).

I claim:
1. A method of isolating chitin, chitin derivatives, and/or chitin-containing microorganisms from a sample, comprising:
contacting a sample with a material having a surface that comprises silica ($SiO_2$), wherein at least part of the $SiO_2$-containing material surface is covered with an acidic solution having a pH of about 2.0 to about 6.0;
wherein the sample contains chitin, a chitin derivative, and/or a chitin-containing microorganism, whereby the chitin, chitin derivative, and/or chitin-containing microorganism binds to the material surface and is thereby isolated from the sample, and wherein the chitin derivative is selected from polymers of β-(1-4)-linked D-glucosamine, polymers of alkyl-substituted β-(1-4)-linked D-glucosamine, chitosan, carboxymethyl chitosan, oleoyl chitosan, hydroxypropyl chitosan, and pegylated chitosan.

2. The method according to claim 1, wherein the material surface comprises glass.

3. The method according to claim 2, wherein the material is selected from glass beads, glass fiber and/or glass matrix.

4. The method according to claim 1, wherein at least part of the $SiO_2$-containing material surface is covered with an acidic solution having a pH of about 2.0 to about 5.0.

5. The method according to claim 1, wherein the material is packed into a chromatographic column as solid phase sorbent material.

6. The method according to claim 5, further comprising:
eluting the chitin, chitin derivative, and/or chitin-containing organism by contacting the material with an alkaline solution; and
recovering the chitin, chitin derivative, and/or chitin-containing microorganism in the alkaline solution.

7. The method according to claim 6, wherein the alkaline solution has a pH of about 7.5 to 9.5.

8. The method according to claim 1, wherein the sample is selected from an environmental sample, water sample, turbid sample, bodily fluid, biopsy, mucus, blood, lymph, serum, plasma, urine, saliva, nasal or ocular fluid, cells, tissue, feces, or stool.

9. The method according to claim 1, wherein the sample contains a chitin-containing microorganism.

10. The method according to claim 9, wherein the chitin-containing microorganism is a fungus species.

11. The method according to claim 10, wherein the chitin-containing microorganism is a microsporidium species.

12. The method according to claim 9, further comprising detecting the chitin-containing microorganism using in-situ immunochemical staining, Western blots, enzyme-linked immunosorbent assay (ELISA), immunoprecipitation, immunofluorescence, radioimmunoassay, immunodot analysis and/or immunocytochemistry.

13. The method according to claim 1, further comprising determining whether the sample contains a chitin-containing microorganism, comprising:

incubating the sample with a primary antibody that specifically binds to the chitin-containing microorganism;
incubating the sample with a secondary antibody that specifically binds to the primary antibody, wherein the secondary antibody is labeled; and
detecting whether the secondary antibody is hound to the material, wherein the binding of the secondary antibody to the material indicates that the sample contain the chitin-containing microorganism.

14. The method according to claim 13, wherein the second antibody is conjugated with an alkaline phosphatase.

15. A method for detecting infection with chitin-containing microorganisms, comprising:
obtaining a biological sample from a subject;
contacting the biological sample with a material having a surface that comprises silica ($SiO_2$), wherein at least part of the $SiO_2$-containing material surface is covered with an acidic solution having a pH of about 2.0 to about 6.0; and
determining the presence or absence of the chitin-containing microorganism in the biological sample using any one or more of in-situ immunochemical staining, Western blots, enzyme-linked immunosorbent assay (ELISA), immunoprecipitation, immunofluorescence, radioimmunoassay, immunodot analysis, and immunocytochemistry;
wherein the presence of the chitin-containing microorganism in the biological sample indicates that the subject has infection.

16. The method according to claim 15, wherein the material surface comprises glass.

17. The method according to claim 15, wherein the material is packed into a chromatographic column as solid phase sorbent material.

18. The method, according to claim 1, further comprising recovering the isolated chitin, chitin derivative, and/or chitin-containing microorganism.

19. The method according to claim 1, wherein the $SiO_2$-containing material surface is soaked in an acidic solution having a pH about 2.0 to about 6.0.

20. The method according to claim 18, wherein the $SiO_2$-containing material surface is soaked in an acidic solution having a pH about 2.0 to about 6.0.

* * * * *

UNITED STATES PATENT AND TRADEMARK OFFICE
CERTIFICATE OF CORRECTION

PATENT NO. : 8,580,934 B2  
APPLICATION NO. : 12/869581  
DATED : November 12, 2013  
INVENTOR(S) : My Lien Dao Page 1 of 1

It is certified that error appears in the above-identified patent and that said Letters Patent is hereby corrected as shown below:

In the Specification

Column 2,  
Line 3, "can not" should read --cannot--.

Figure 1:
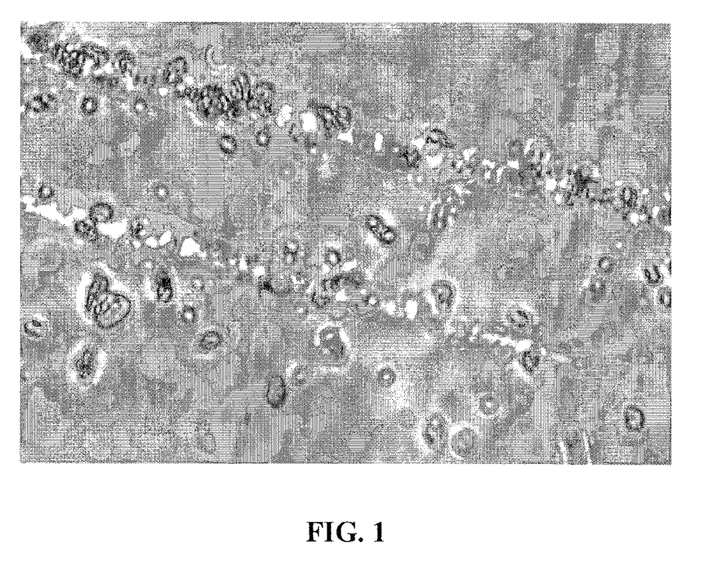
FIG. 1 shows spores of chitin-containing microorganisms isolated from blood samples. Spores were isolated using affinity chromatographic columns packed with glass beads treated with 10% acetic acid, and stained for observation by the methods described in Dao (U.S. Pat. Nos. 7,157,242 and 7,745,168).
Figure 2:
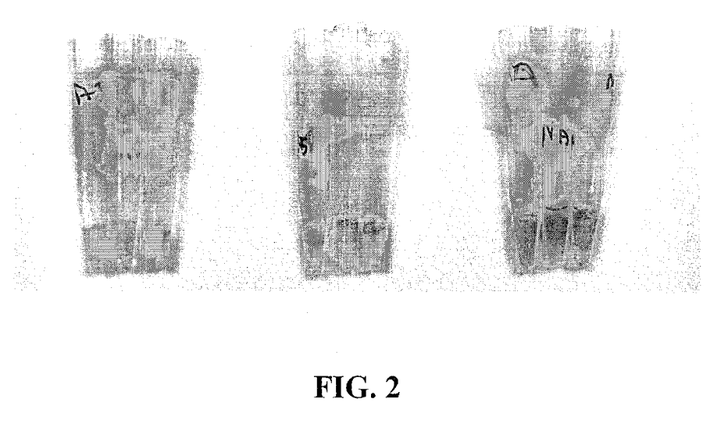
Figure 3:
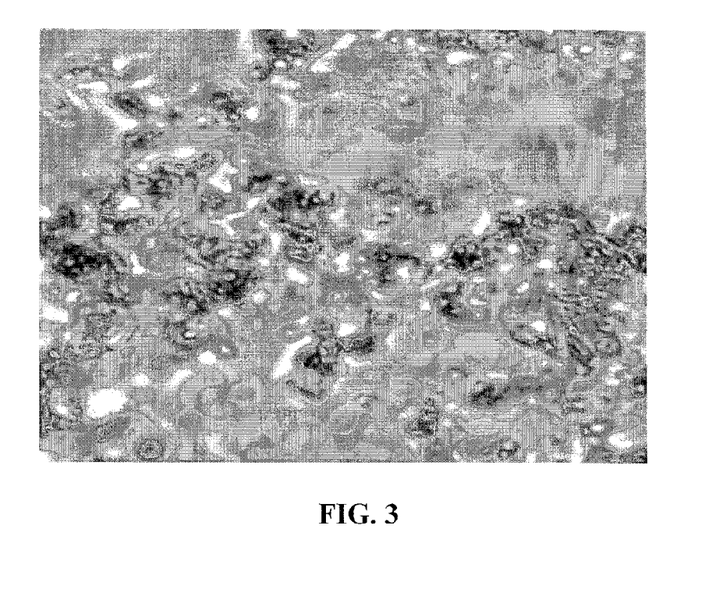
FIG. 3 shows spores of microsporidia *Encephalitozoon* eluted from the immunochemically-stained column packed with glass fiber.
Figure 4:
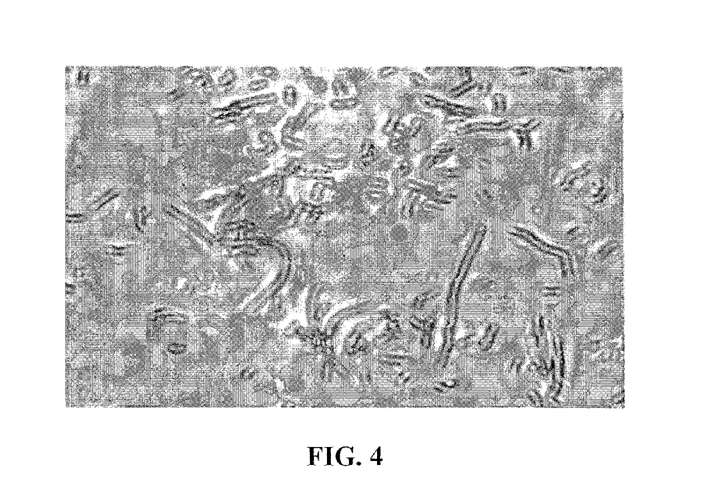
FIG. 4 shows chitin-containing spores, which were obtained from cell culture infected with chitin-containing microorganism spores isolated from blood samples of infected individuals. RK13 cells were infected with chitin-containing microorganisms and spores were isolated at day 10 post-infection. Spores were stained for observation by the methods described in Dao (U.S. Pat. Nos. 7,157,242 and 7,745,168). The image shows single spores and spores at developmental stages, which are in a form of ribbon-like chains (monoliforms).

Column 3,  
Line 10, "FIG 2" should read --FIG. 1--.  
Line 12, "spores hound" should read --spores bound--.  
Line 26, "FIG. 1" should read --FIG. 2--.

Column 11,  
Line 22, "PH 9.7)." should read --pH 9.7).--.

In the Claims

Column 16, Claim 13,  
Line 6, "is hound" should read --is bound--.  
Line 8, "sample contain" should read --sample contains--.

Signed and Sealed this  
First Day of July, 2014

Michelle K. Lee  
*Deputy Director of the United States Patent and Trademark Office*